United States Patent [19]

McCoy et al.

[11] Patent Number: 4,558,159
[45] Date of Patent: Dec. 10, 1985

[54] POLYETHER BIGUANIDE SURFACTANTS

[75] Inventors: David R. McCoy; Carter G. Naylor, both of Austin, Tex.

[73] Assignee: Texaco Inc., White Plains, N.Y.

[21] Appl. No.: 614,611

[22] Filed: May 29, 1984

[51] Int. Cl.$^4$ ............................................. C07C 129/16
[52] U.S. Cl. ..................................... 564/233; 564/234; 8/142; 252/106; 252/153; 252/544; 252/DIG. 13
[58] Field of Search ................................ 564/233, 234

[56] References Cited

U.S. PATENT DOCUMENTS

| | | | |
|---|---|---|---|
| 3,909,200 | 9/1985 | Redmore | 252/390 |
| 4,403,078 | 9/1983 | McCoy et al. | 525/504 |
| 4,405,645 | 9/1983 | Röthlisberger et al. | 424/326 |

Primary Examiner—Natalie Trousof
Assistant Examiner—Leah Hendriksen
Attorney, Agent, or Firm—Jack H. Park; Kenneth R. Priem; Richard A. Morgan

[57] ABSTRACT

Polyether biguanide salts of the formula:

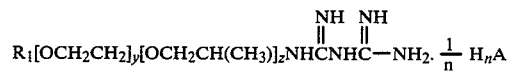

wherein:
- y ranges from 0 to 6,
- z ranges from 2 to 7,
- A is an anion selected from the group consisting of chloride, bromide, sulfate, bisulfate, phosphate, dihydrogen phosphate and hydrogen phosphate,
- n is the valence of the anion, and
- $R_1$ is an alkyl of 9 to 18 carbon atoms or alkylphenyl of 15 to 18 carbon atoms, are diluted in water solution. In a preferred embodiment, $R_1$ is nonylphenyl.

These salts are surface active agents used as hair conditioning agents, foam boosters, corrosion inhibitors, ore flotation agents, fabric softeners or germicides, etc.

10 Claims, No Drawings

POLYETHER BIGUANIDE SURFACTANTS

BACKGROUND OF THE INVENTION

1. Field of the Invention

This invention relates to a series of surface active polyether biguanide salts. The invention also relates to a series of water solutions of surface active polyether biguanide salts.

2. Description of the Prior Art

The term surfactant refers to substances which lower liquid-liquid, liquid-solid or liquid-gas interfacial tension. Surfactant solutions used by themselves or in conjunction with cleaning adjuvants such as additives or builders are widely used to wet surfaces, remove soil, penetrate porous materials, disperse particles, emulsify oils and greases, etc., dependent upon the particular characteristics of the surfactant or surfactants used.

Desirably surfactants are inexpensive, light colored materials which function at low concentration levels in aqueous solutions and which can be produced in good yield from readily available low cost starting materials, free from deleterious contaminants, preferably as easily handled, free-flowing liquids or powders.

For many applications, such as heavy duty industrial applications for metal scouring and dishwasher detergent compositions, the compositions necessarily include highly alkaline materials such as alkali metal hydroxides, alkoxides and phosphates. In the aqueous media that these detergents function, the pH of the cleaning solution frequently will be from 10 to 13. For this reason a prerequisite of heavy duty detergency compositions is stability at elevated pH's in aqueous solutions.

It has been found, surprisingly, that certain polyether biguanide epoxy curative agents described in U.S. Pat. No. 4,403,078 display surface activity in water solution.

SUMMARY OF THE INVENTION

This invention relates to a series of polyether biguanide salts which find use as detergents. The composition of matter of the present invention is characterized by the general formula:

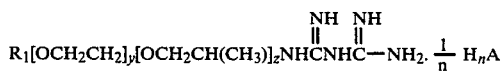

wherein:
y ranges from 0 to 6,
z ranges from 2 to 50,
A is an anion selected from the group consisting of chloride, bromide, sulfate, bisulfate, phosphate, dihydrogen phosphate, and hydrogen phosphate,
n is the valence of the anion and
$R_1$ is selected from the group consisting of alkyl and alkylphenyl each of 1 to 24 carbon atoms; with the proviso that when z ranges from 2 to 14, $R_1$ is limited to 8 to 24 carbon atoms and when z ranges from 15 to 50, $R_1$ is limited to 1 to 7 carbon atoms.

These compositions of matter have a variety of uses. These uses include hair conditioning agents, foam boosters and fabric softeners.

DETAILED DESCRIPTION OF THE INVENTION

Polyether biguanide salts are the surfactants of the present invention. These surfactants are prepared essentially in two steps. A method is fully described in U.S. Pat. No. 3,909,200 which is incorporated herein in its entirety by reference.

In the first step a salt is prepared from a polyoxyalkylene momoamine of the formula:

wherein:
y ranges from 0 to 6,
z ranges from 2 to 50, and
$R_1$ is selected from the group consisting of alkyl and alkylphenyl each of 1 to 24 carbon atoms; with the proviso that when z ranges from 2 to 14, $R_1$ is limited to 8 to 24 carbon atoms and when z ranges from 15 to 50, $R_1$ is limited to 1 to 7 carbon atoms. When $R_1$ is alkyl the alkyl is preferably normal. When $R_1$ is alkylphenyl the alkyl is preferably branched.

In the alternative, in solutions of the present invention, a polyoxypropylenediamine may be utilized as a starting material. This diamine is of the general formula:

wherein:
x ranges from 15 to 90, preferably 30 to 40.

As stated, a salt is prepared from the monoamine or diamine as previously defined with a desired acid of an appropriate ratio of one equivalent of acid for every amine functionality, to produce an amine salt.

In a second step, the salt is treated with a slight molar excess (based on amine groups present) of dicyandiamide (cyanoguanidine) and heated in the presence or absence of added solvent at about 100° C. to 200° C. (preferably 150° C.) for 1 to 10 hours until the biguanide salt is formed.

Inorganic salts such as HCl or $H_2SO_4$ are preferred for this reaction. It has been found to be necessary to neutralize each amine functionality with an equivalent of acid for the biguanide formation to take place. Excess acid can be employed but is not desirable. Less than one mole of acid/mole of amine can be utilized only if a di- or tri-basic acid is used.

The compositions of matter are then diluted to the desired strength. It has been found that the most cost effective dilution is 0.01 wt% to 20 wt% preferably 0.1 wt% to 5 wt% with a water diluent. In this regard, the present invention is:

An aqueous solution comprising:

A. 0.01 wt% to 20 wt% preferably 0.1 wt% to 5 wt% of a composition of matter of the general formula:

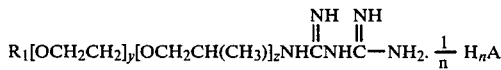

wherein:
y ranges from 0 to 6,
z ranges from 2 to 50,
A is an anion selected from the group consisting of chloride, bromide, sulfate, bisulfate, phosphate, dihydrogen phosphate, and hydrogen phosphate,
n is the valence of the anion, and
$R_1$ is selected from the group consisting of alkyl and alkylphenyl each of 1 to 24 carbon atoms with the proviso that when z ranges from 2 to 14, $R_1$ is limited to 8 to 24 carbon atoms and when z ranges from 15 to 50, $R_1$ is limited to 1 to 7 carbon atoms; and B. water.

This invention is also an aqueous solution comprising:

A. 0.01 wt% to 20 wt% preferably 0.1 wt% to 5 wt% of a composition of matter of the general formula:

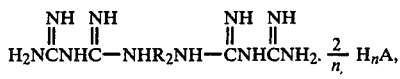

wherein:

A is an anion selected from the group consisting of chloride, bromide, sulfate, bisulfate, phosphate, dihydrogen phosphate, and hydrogen phosphate, n is the valence of the anion, $R_2$ is a polyxoypropylene radical of the formula:

wherein:

x ranges from 15 to 90 preferably 30 to 40; and

B. water.

The polyether biguanide salts exhibit long lasting surfactant properties in aqueous solution in concentrations ranging from 0.01 wt% and higher depending upon the mode of application. The minimal concentration of ethoxylated product usually employed is about 0.01 wt% while the upper concentration, which is limited almost entirely by cost, for all but special purposes seldom exceeds 20 wt%. Usually the range of concentration is between about 0.1 wt% to 5 wt% with the residuum being detergent adjuvants described below. In all instances the lower or minimal concentration (0.01% by weight) is referred to as an "effective amount" of surfactant. When these products are employed as detergents they ordinarily are present in at least the minimal concentrations disclosed accompanied by one or more of the following classes of materials which are generically referred to as detergent adjuvants:

1. Inorganic salts, acids and bases. These are usually referred to as "builders." These salts usually comprise alkalies, phosphates and silicates of the alkali metals as well as their neutral soluble salts. These materials constitute from about 40 to 80 weight percent of the composition in which they are employed.

2. Organic builders or additives—These are substances which contribute to characteristics such as detergency, foaming power, emulsifying power or soil suspending effect. Typical organic builders include sodium carboxymethyl cellulose, sequestering agents such as ethylenediaminetetraacetic acid and the fatty monoethanolamides, etc.

3. Special purpose additives—These include solubilizing additives such as lower alcohols, glycols and glycol ethers, bleaches or brighteners of various structures which share in common that they are dyestuffs and they do not absorb or reflect light in the visible range of the spectrum.

DETERGENT FORMULATIONS

A. Dry cleaning composition

| Parts by wt. | Components |
| --- | --- |
| 5 | SURFONIC ® N-40 (average 4 molar ethoxylate of nonylphenol) |
| 5 | Product Example E |
| 60 | Dry cleaning solvent |
| 30 | Water |

B. Disinfectant and Detergent Composition

-continued
DETERGENT FORMULATIONS

| Parts by wt. | Component |
| --- | --- |
| 5 | Product of Example C |
| 5 | EDTA |
| 88 | 10% Hydrochloric Acid |
| 2 | SURFONIC ® N-95 (average 9.5 molar ethoxylate of nonylphenol) |

C. Shampoo

| Parts by wt. | Component |
| --- | --- |
| 5 | Product of Example A |
| 5 | Cocoamide DEA |
| 20 | Sodium lauryl sulfate |
| 70 | Water |

In regard to actual use of the composition of matter of the present invention particularly in water base solutions, it has been found that a favorable cost to benefit ratio is achieved when $R_1$ is a normal alkyl of from 9–18 carbon atoms or $R_1$ is alkylphenyl selected from the group consisting of nonylphenyl, decylphenyl, undecylphenyl and dodecylphenyl.

Further in regard to actual use, criticality has been found in the parameter x. Surface activity is found in the range of x from 15 to 90. Excellent surfactant properties are demonstrated when x ranges from 30 to 40 as shown in Example F.

This invention is better shown by way of example.

EXAMPLE A (1) A one-liter resin flask equipped with mechanical stirrer, thermometer and nitrogen inlet was charged with 618 grams of JEFFAMINE ® D-2000 and 61 grams concentrated hydrochloric acid. The mixture was vacuum stripped at 100° C. to remove all traces of water. Dicyandiamide (65.2 grams; 1.25 equivalents) was added and the mixture was stirred under nitrogen atmosphere for seven hours to obtain the desired bis(biguanide) hydrochloride salt; identified by total amine analysis and infrared spectrum as:

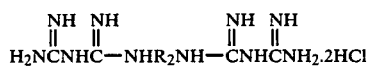

wherein $R_2$ is:

(2) One hundred grams of the hydrochloride salt of D-2000 bis(biguanide), prepared according to A (1), was treated with 6.8 g 50% aqueous sodium hydroxide solution and heated with mechanical stirring at 100° C. for one hour. The mixture was vacuum stripped to remove water and filtered to remove sodium chloride. The free biguanide filtrate contained only 0.43% Cl and was insoluble (1 wt% would not dissolve in water at 25° C.).

JEFFAMINE ® D-2000 is the diterminal diamine of polyoxypropylene of molecular weight 2000 of the general formula:

EXAMPLE B

Charged 1-liter flask with 657 grams JEFFAMINE ® M-1000 and added 64.8 g concentrated hydrochloric acid. Water was removed under reduced pressure at 100° C., system was purged with nitrogen, and 69 g (1.25 equiv.) dicyandiamide was added with mechanical stirring. The mixture was heated to 150° C. and stirred under nitrogen atmosphere for an additional 6 hours. Product was identified as the desired biguanide hydrochloride salt by elemental and spectral analyses. Structure was:

JEFFAMINE ® M-1000 is a monoamine of molecular weight 1000 of the general formula:

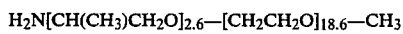

EXAMPLE C

Method of Example B was used with 278 g JEFFAMINE ® M-300, 100 g conc. HCl, and 105 g dicyandiamide.

Product was identified as the desired biguanide hydrochloride salt by elemental and spectral analysis as:

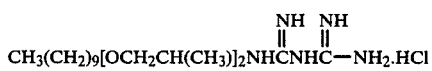

JEFFAMINE ® M-300 is a monoamine of the general formula:

EXAMPLE D

The method of Example B was used with 600 grams JEFFAMINE ® M-600, 100 grams concentrated HCl and 205 grams dicyandiamide.

Product was identified as the desired biguanide hydrochloride salt by elemental and spectral analysis as:

JEFFAMINE ® M-600 is a monoamine of molecular weight 600 of the general formula:

EXAMPLE E

Method of Example B was used with 78 g dicyandiamide, 74.5 g conc. HCl, and

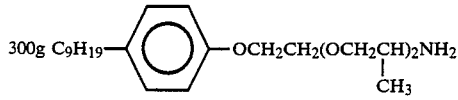

Product was identified as the desired biguanide hydrochloride salt by elemental and spectral analysis as:

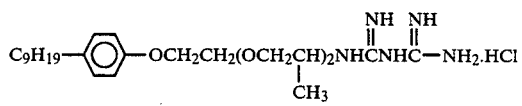

EXAMPLE F

The surface active properties of water solutions of the products of Examples A, B, C, D and E are reported in Table 1. The surfactant properties of Examples A, C and E are good to excellent, while those of Examples B and D which are outside the scope of the present invention are weak. Criticality has been found in the ratio of the amount of propylene oxide to the size of the terminal alkyl or alkylaryl group. When this terminal alkyl or alkylaryl group is 1 to 7 carbon atoms, the amount of propylene oxide must be increased to 15 to 50 molecules per surfactant molecule to reduce water solubility and thereby increase surface activity. When this group is 8 carbon atoms or greater, the amount of propylene oxide must be reduced 2 to 14 molecules per surfactant molecule to increase water solubility (decrease oil solubility) and thereby increase surface activity. Further, ethylene oxide is added for water solubility in an amount of 0 to 6 molecules per surfactant molecule to balance the effect of propylene oxide and thereby give the molecule its characteristic surface activity. This discovered criticality is expressed as defined herein and in the claims. The wetting ability of the surfactants of Examples A, C and E is somewhat low due to their cationic nature. The good surfactant effectiveness is due to the hydrophobic portion of the biguanide surfactant.

TABLE 1

Surface-Active Properties of Bis(biguanides) and Biguanides

| Product of Example | Surface Tension dynes/cm | | Interfacial Tension dynes/cm | | Ross-Miles Foam Height, mm (120° F.) | | | | Draves Wetting, sec. (0.1%) | |
|---|---|---|---|---|---|---|---|---|---|---|
| | | | | | 0.1% | | 1.0% | | | |
| | 0.1% | 1.0% | 0.1% | 1.0% | 0 | 5 min | 0 | 5 min | 1.5 g hook | 3 g hook |
| A | 36.4 | 34.2 | 6.2 | 3.2 | 74 | 16 | 135 | 22 | — | 39 |
| B | 57.1 | 46.3 | 25.1 | 25.4 | — | — | — | — | — | — |
| C | 29.6 | 26.5 | 1.5 | 1.6 | 126 | 85 | — | — | 139 | 49 |
| D | 46.3 | 41.4 | 16.3 | 12.2 | 0 | 0 | — | — | — | >180 |
| E | 29.5 | 28.6 | 1.2 | 1.2 | 124 | 80 | 149 | 115 | — | — |

The principle of the invention and the best mode contemplated for applying that principle have been described. It is to be understood that the foregoing is illustrative only and that other means and techniques can be employed without departing from the true scope of the invention defined in the following claims:

What is claimed is:

1. A composition of mater of the formula:

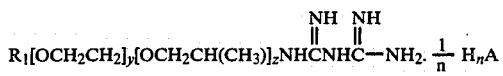

wherein:
y ranges from 0 to 6,
z ranges from 2 to 14,
A is an anion selected from the group consisting of chloride, bromide, sulfate, bisulfate, phosphate, dihydrogen phosphate and hydrogen phosphate,
n is the valence of the anion and
$R_1$ is selected from the group consisting of alkyl and alkylphenyl each of 8 to 24 carbon atoms.

2. The composition of matter of claim 1 wherein z ranges from 2 to 7.

3. The composition of matter of claim 1 wherein $R_1$ is an alkyl of 9 to 18 carbon atoms.

4. The composition of matter of claim 1 wherein $R_1$ is an alkylphenyl selected from the group consisting of nonylphenyl, decylphenyl, undecylphenyl and dodecylphenyl.

5. The composition of matter of claim 1 wherein $R_1$ is dodecylphenyl.

6. The composition of matter of claim 1 wherein $R_1$ is nonylphenyl.

7. A composition of matter of the formula:

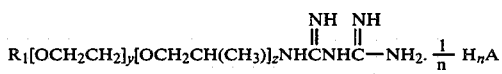

wherein:
y ranges from 0 to 6,
z ranges from 15 to 50,
A is an anion selected from the group consisting of chloride, bromide, sulfate, bisulfate, phosphate, dihydrogen phosphate and hydrogen phosphate,
n is the valence of the anion and
$R_1$ is an alkyl of 1 to 7 carbon atoms.

8. The composition of matter of claim 7 wherein $R_1$ is an alkyl of 1 to 4 carbon atoms.

9. An aqueous solution comprising:
A. 0.1 wt% to 20 wt% of a composition of matter of the formula:

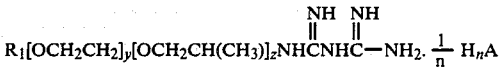

wherein:
y ranges from 0 to 6,
z ranges from 2 to 50,
A is an anion selected from the group consisting of chloride, bromide, sulfate, bisulfate, phosphate, dihydrogen phosphate and hydrogen phosphate;
n is the valence of the anion, and
$R_1$ is selected from the group consisting of alkyl and alkylphenyl each of 1 to 24 carbon atoms with the proviso that when z ranges from 2 to 14, $R_1$ is limited to 8 to 24 carbon atoms and when z ranges from 15 to 50, $R_1$ is limited to 1 to 7 carbon atoms; and
B. water.

10. The solution of claim 9 wherein the composition of matter comprises 0.1 wt% to 5 wt%.

* * * * *